United States Patent
Oouchi

(10) Patent No.: US 8,459,862 B2
(45) Date of Patent: Jun. 11, 2013

(54) STIRRING DEVICE, MICROBE TESTING DEVICE, AND MICROBE TESTING METHOD

(75) Inventor: Kazufumi Oouchi, Ehime (JP)

(73) Assignee: Panasonic Corporation, Osaka (JP)

( * ) Notice: Subject to any disclaimer, the term of this patent is extended or adjusted under 35 U.S.C. 154(b) by 702 days.

(21) Appl. No.: 12/397,559

(22) Filed: Mar. 4, 2009

(65) Prior Publication Data

US 2009/0223824 A1 Sep. 10, 2009

(30) Foreign Application Priority Data

Mar. 5, 2008 (JP) ................................. 2008-054700
Mar. 5, 2008 (JP) ................................. 2008-055603

(51) Int. Cl.
*G01N 27/447* (2006.01)
*B01F 13/08* (2006.01)

(52) U.S. Cl.
USPC ............ 366/273; 366/274; 366/279; 366/341

(58) Field of Classification Search
USPC ................... 366/273, 274, 279, 341
See application file for complete search history.

(56) References Cited

U.S. PATENT DOCUMENTS

| | | | | |
|---|---|---|---|---|
| 2,466,468 A | * | 4/1949 | Neal | 366/274 |
| 3,168,294 A | * | 2/1965 | Hasumura | 366/206 |
| 3,245,665 A | * | 4/1966 | Steel | 416/3 |
| 3,645,508 A | * | 2/1972 | Balteau | 366/273 |
| 3,661,302 A | * | 5/1972 | Braun | 222/226 |
| 4,836,826 A | * | 6/1989 | Carter | 464/29 |
| 5,176,446 A | * | 1/1993 | Chiba et al. | 366/114 |
| 5,240,322 A | * | 8/1993 | Haber et al. | 366/130 |
| 5,803,137 A | * | 9/1998 | Shimotoyodome et al. | 141/67 |
| 5,961,213 A | * | 10/1999 | Tsuyuki et al. | 366/273 |
| 5,985,535 A | * | 11/1999 | Urabe | 430/569 |
| 6,176,609 B1 | * | 1/2001 | Cleveland et al. | 366/273 |
| 6,273,600 B1 | | 8/2001 | Sharpe | |
| 6,712,497 B2 | * | 3/2004 | Jersey et al. | 366/274 |
| 6,733,171 B2 | * | 5/2004 | Schob | 366/273 |
| 7,481,572 B2 | * | 1/2009 | Terentiev | 366/279 |
| 8,162,532 B2 | * | 4/2012 | Toole | 366/165.2 |
| 2002/0118594 A1 | * | 8/2002 | Vellinger et al. | 366/116 |
| 2002/0196705 A1 | * | 12/2002 | Jersey et al. | 366/274 |
| 2003/0053371 A1 | * | 3/2003 | Schoeb | 366/273 |
| 2003/0107950 A1 | * | 6/2003 | Shepherd et al. | 366/317 |
| 2004/0165477 A1 | * | 8/2004 | Long | 366/273 |
| 2005/0002274 A1 | * | 1/2005 | Terentiev | 366/273 |
| 2005/0117449 A1 | * | 6/2005 | Terentiev | 366/273 |
| 2006/0092761 A1 | * | 5/2006 | Terentiev | 366/274 |
| 2009/0078619 A1 | * | 3/2009 | Hidaka et al. | 209/659 |
| 2009/0129201 A1 | * | 5/2009 | Terentiev | 366/273 |
| 2010/0264090 A1 | * | 10/2010 | Ellis et al. | 210/695 |
| 2010/0290308 A1 | * | 11/2010 | Terentiev | 366/143 |
| 2012/0171718 A1 | * | 7/2012 | Le et al. | 435/41 |

FOREIGN PATENT DOCUMENTS

| | | |
|---|---|---|
| JP | 06-343844 | 12/1994 |
| JP | 11-244681 | 9/1999 |

(Continued)

*Primary Examiner* — Joseph S Del Sole
*Assistant Examiner* — Nahida Sultana
(74) *Attorney, Agent, or Firm* — Wenderoth, Lind & Ponack, L.L.P.

(57) ABSTRACT

A microbe testing device includes a measurement cell for holding a sample liquid, and a rotor that is rotated, by magnetic force imparted from outside the measurement cell, along a bottom face in the sample liquid held in the measurement cell. The sample liquid is stirred by rotating the rotor so that only its end portions are in contact with the bottom face of the measurement cell.

10 Claims, 7 Drawing Sheets

FOREIGN PATENT DOCUMENTS

| | | |
|---|---|---|
| JP | 2000-509989 | 8/2000 |
| JP | 2003-000224 | 1/2003 |
| JP | 2005-169303 | 6/2005 |
| JP | 2006-098077 | 4/2006 |
| JP | 2009-207431 | 9/2009 |

* cited by examiner

STIRRING DEVICE, MICROBE TESTING DEVICE, AND MICROBE TESTING METHOD

CROSS-REFERENCE TO RELATED APPLICATIONS

This application claims priority to Japanese Patent Application Nos. 2008-055603 and 2008-054700. The entire disclosures of Japanese Patent Application Nos. 2008-055603 and 2008-054700 are hereby incorporated herein by reference.

BACKGROUND OF THE INVENTION

1. Technical Field

The present invention relates to a stirring device for stirring a sample liquid by rotating a rotor in a sample liquid that is held inside a case.

2. Description of the Related Art

Stirring devices that stir a sample liquid while a rotor is rotated in a liquid contained in a case by magnetic force imparted from outside the case have been used in recent years in the reaction analysis of microbes and other such specimens included in a sample liquid.

For example, Patent Document 1 (Japanese Laid-Open Patent Application 2005-169303) discloses a stirring vessel in which a support portion (convex portion) that serves as the rotational center of a stirrer (rotor) is provided to the bottom face of a vessel (case). With this constitution, the stirrer is rotated so as to be away from the bottom of the vessel, which reduces the rotational resistance in the sample liquid, and allowing smoothly driven rotation to be performed by a magnet rotary body disposed outside the vessel.

SUMMARY

However, the following problems are encountered with the conventional stirring vessel discussed above.

With the constitution disclosed in the above-mentioned publication, because a convex portion is provided in the approximate center of the bottom, there are cases when the rotating rotor becomes unbalanced and falls off the convex portion due to the load produced by contact with solids or the like in the sample liquid, or to a viscosity difference of the sample liquid. In such cases, there is the risk that rotation of the rotor will be insufficient, or that the rotation of the rotor will come to a complete stop, and the sample liquid cannot be adequately stirred.

It is an object of the present invention to provide a stirring device with which the rotor can be stably rotated regardless of the conditions in the sample liquid, etc.

Means for Solving Problem

The stirring device pertaining to the first aspect of the invention comprises a case and a rotor. The case holds a sample liquid. The rotor stirs the sample liquid by being rotated by magnetic force, imparted from outside the case, along the inner wall face of the case in the sample liquid held inside the case, with only the two end portions of the rotor coming into contact with the inner wall face of the case.

Here, with a microbe testing device in which an electrode portion for detecting microbes by electrophoresis and a rotor for stirring a sample liquid are disposed inside a case that holds a sample liquid, the rotor rotates while in contact only at its two end portions with the inner wall face (rotation face) inside the case in which the rotor rotates.

Here, the idea that the rotor and the inner wall face of the case only come into contact at the two end portions of the rotor can be either a configuration in which a concave portion is formed in the center portion of the inner wall face of the case, or a configuration in which a large diameter portion is formed at the two ends of the rotor, or a combination of these. Also, the inner wall face inside the case in which the rotor rotates includes the bottom face, side face, etc., inside the case. If the rotational resistance of the rotor is greater than with a conventional configuration in which a central convex portion serves as the rotational axis, the same rotational speed as in the past can be ensured by increasing the magnetic force imparted to the rotor.

Consequently, the ends of the rotor can be supported with good balance while entailing frictional resistance at the portions of the rotor ends that come into contact with the inner wall face. Thus, even if there is a large viscosity difference in the sample liquid, or if solids or the like should be admixed in the sample liquid, the rotating rotor will not lose its rotational balance under external load. As a result, compared to a conventional stirring device in which the rotor is rotated around a protrusion formed on the inner wall face of the case, it is easier to reach balance in the rotation of the rotor, so the sample liquid can be sufficiently stirred regardless of the conditions of the sample liquid, etc.

The stirring device pertaining to the second aspect of the invention is the stirring device pertaining to the first aspect of the invention, wherein the inner wall face has a concave portion formed around the rotational axis of the rotor.

Here, a concave portion whose center is the rotational center around which the rotor rotates is provided on the inner wall face side as a means for constituting a mode for bringing the rotor into contact with the inner wall face only at its ends.

Consequently, because the concave portion is provided on the opposite side from that of a conventional stirring device in which a convex portion was provided to the portion of the inner wall face serving as the rotational center of the rotor, the ends of the rotor are securely supported in the region outside of the concave portion of the inner wall face, while the rotor can be rotated in a stable state.

The stirring device pertaining to the third aspect of the invention is the stirring device pertaining to the second aspect of the invention, wherein the concave portion is formed in a size such that even when the rotor has moved to an offset position along the inner wall face inside the case, the end on the opposite side from the offset side will not fall into the concave portion.

Here, the size of the concave portion is set on the basis of the axial length of the rotor, taking into account the occurrence of problems caused by providing a concave portion to the inner wall face.

Specifically, in order to keep the rotor from getting stuck in the concave portion provided to the inner wall face, the size of the concave portion is set such that one end of the rotor will not fall into the concave portion even if the rotor moves to an offset position along the inner wall face.

Consequently, even if the rotor should move to an offset position along the inner wall face of the case, for example, the rotor can be disposed in a state of always being supported at its two ends on the inner wall face. As a result, the rotor is able to rotate more smoothly within the case.

The stirring device pertaining to the fourth aspect of the invention is the stirring device pertaining to the second or third aspect of the invention, wherein the inner wall face is the substantially circular bottom face of the case, and the concave portion is formed so that its diameter d satisfies the following Relational Formula 1 with the diameter D of the substantially circular inner wall face.

$$0.3D \leq d \leq 0.9D \quad (1)$$

Here, the diameter of the substantially circular concave portion formed in the inner wall face where the rotor rotates is set on the basis of the bottom face of the case.

The phrase "substantially circular" as used above encompasses polyhedral shapes that are not completely circular, but whose overall shape is circular.

Consequently, the load (frictional resistance) to which the rotor is subjected during rotation can be kept to a suitable level, and a good balance can also be ensured during rotation.

The stirring device pertaining to the fifth aspect of the invention is the stirring device pertaining to any of the first to fourth aspects of the inventions, wherein the rotor has a large diameter portion at both end portions.

Here, a large diameter portion is provided to the end portions of the rotor as a mode for bringing only the ends of the rotor into contact with a specific inner wall face of the case when the rotor rotates on this inner wall face.

Here, the large diameter portion may be formed by integral molding of the entire rotor, or may be formed by post-working of the joints of parts, etc., with respect to substantially cylindrical or substantially prismatic members.

With the present invention, the formation of the large diameter portion may also be combined with the formation of a concave portion in the inner wall face.

Consequently, the portions where the rotor and the inner wall face come into contact can be just the ends of the rotor, without having to modify the shape of the case. As a result, the ends of the rotor can be supported by part of the inner wall face, while the rotor can be rotated with good balance.

The microbe testing device pertaining to the sixth aspect of the invention comprises the stirring device according to any of the first to fifth aspects of the inventions, and an electrode portion provided inside the case, to which is applied voltage for measuring the microbes in the sample liquid by electrophoresis.

Here, the above-mentioned stirring device is provided as a microbe testing device.

Consequently, the sample liquid can be sufficiently stirred by the rotor rotating along the inner wall face in an attitude in which balance tends to be maintained. As a result, stirring accuracy is improved, so that accurate microbe detection can be carried out.

The microbe testing device pertaining to the seventh aspect of the invention is the microbe testing device pertaining to the sixth aspect of the invention, further comprising a sample collector that comes into contact with the rotor that is rotating in the sample liquid, and suspends collected microbes in the sample liquid.

Here, with a microbe testing device in which the above-mentioned stirring device has been installed, microbes are stirred in a sample liquid by immersing a sample collector that collects microbes into the sample liquid and stirring with a rotor. When the sample collector is immersed into the sample liquid, part of the sample collector hits the rotating rotor.

Here, a cotton swab or the like that collects microbes, etc., in the oral cavity can be used, for example, as the above-mentioned sample collector.

Consequently, microbes adhering to the distal end, etc., of the sample collector can be effectively stirred in the sample liquid. As a result, a microbe testing device can be obtained with which microbes can be accurately detected from a sample liquid that has been effectively stirred.

The microbe testing method pertaining to the eighth aspect of the invention comprises first to fourth steps in a microbe testing method in which a sample collector in which a sample has been collected is inserted into a sample liquid contained inside a case, and the sample liquid is stirred by the rotor while microbes are detected. In the first step, the distal end of the sample collector is inserted into the sample liquid. In the second step, the sample collector in the sample liquid is brought into contact with the rotating rotor. In the third step, the microbes that have been dissolved out of the sample liquid by contact with the rotor are suspended in the sample liquid by rotating of the rotor. In the fourth step, the microbes suspended in the sample liquid X are detected.

Here, for example, when microbes collected in the oral cavity are collected with the sample collector, and the distal end of the sample collector is inserted into the sample liquid, the sample collector is brought into contact with the rotor that is rotating in the sample liquid. The microbes released into the sample liquid are then suspended in the sample liquid by rotating the rotor.

Here, the rotor is rotated by magnetic force imparted from the outside, and the microbes, etc., are suspended in the sample liquid. The sample collector can be, for example, a cotton swab or the like for collecting microbes in the oral cavity.

Consequently, because release and stirring of the microbes collected with the sample collector in the sample liquid are performed at substantially the same time, effective stirring and accurate microbe detection can both be accomplished at a high level in the microbe testing device, without having to use a separate stirring device to carry out effective stirring. As a result, the process from stirring up to microbe testing is simplified, and the cost entailed by microbe testing can be greatly reduced.

The microbe testing method pertaining to the ninth aspect of the invention is the microbe testing method pertaining to the eighth aspect of the invention, wherein, in the second and third steps, the rotor is rotated in the sample liquid while its end portions are brought into contact with the inner wall face of the case.

Here, the rotor that is brought into contact with the sample collector during rotation is rotated so as to come into contact with the inner wall face of the case at the end portions of the rotor.

Consequently, a loss of balance during rotation caused by contact with the sample collector can be prevented by supporting on the inner wall face the end portions of the rotor that is rotating to stir the sample liquid. As a result, the rotor performs two functions, namely, stirring the sample liquid and extracting microbes from the sample collector.

The microbe testing method pertaining to the tenth aspect of the invention is the microbe testing method pertaining to the eighth or ninth aspect of the invention, wherein the sample collector includes a cotton swab.

Here, a cotton swab is used as the sample collector for collecting microbes in the oral cavity, for example.

Consequently, the user performing the microbe test uses an inexpensive and easy-to-use cotton swab to collect microbes, and effectively releases the microbes adhering to the tip of the cotton swab into the sample liquid by contact with the rotor.

DETAILED DESCRIPTION OF THE INVENTION

A microbe testing device 10 for implementing the microbe testing method pertaining to an embodiment of the present invention will now be described through reference to FIGS. 1 to 6.

Plaque and microbes (microorganisms) in the oral cavity, which are the test objects of the microbe testing device 10 in this embodiment, will be described at this point.

Specifically, the primary cause of all the major diseases seen in the oral cavity (such as caries or periodontal disease) is microbes (microorganisms) in the oral cavity. Plaque results when oral microbes cluster locally due to proliferation, and other than the metabolites of polysaccharides and so forth, most of plaque is a clump of microorganisms. The number of microorganisms in one gram of plaque can actually be as high as ten to the tenth or eleventh power. Removing plaque from the oral cavity (hereinafter referred to as plaque control) is that most important factor in maintaining good oral hygiene, and more specifically, brushing is the main approach to plaque control.

Because nearly all oral diseases are thus brought on by the presence of plaque, accurately testing the state of oral hygiene is extremely important in terms of effectively preventing oral disease.

Overall Configuration of Microbe Testing Device 10

Figure 1:
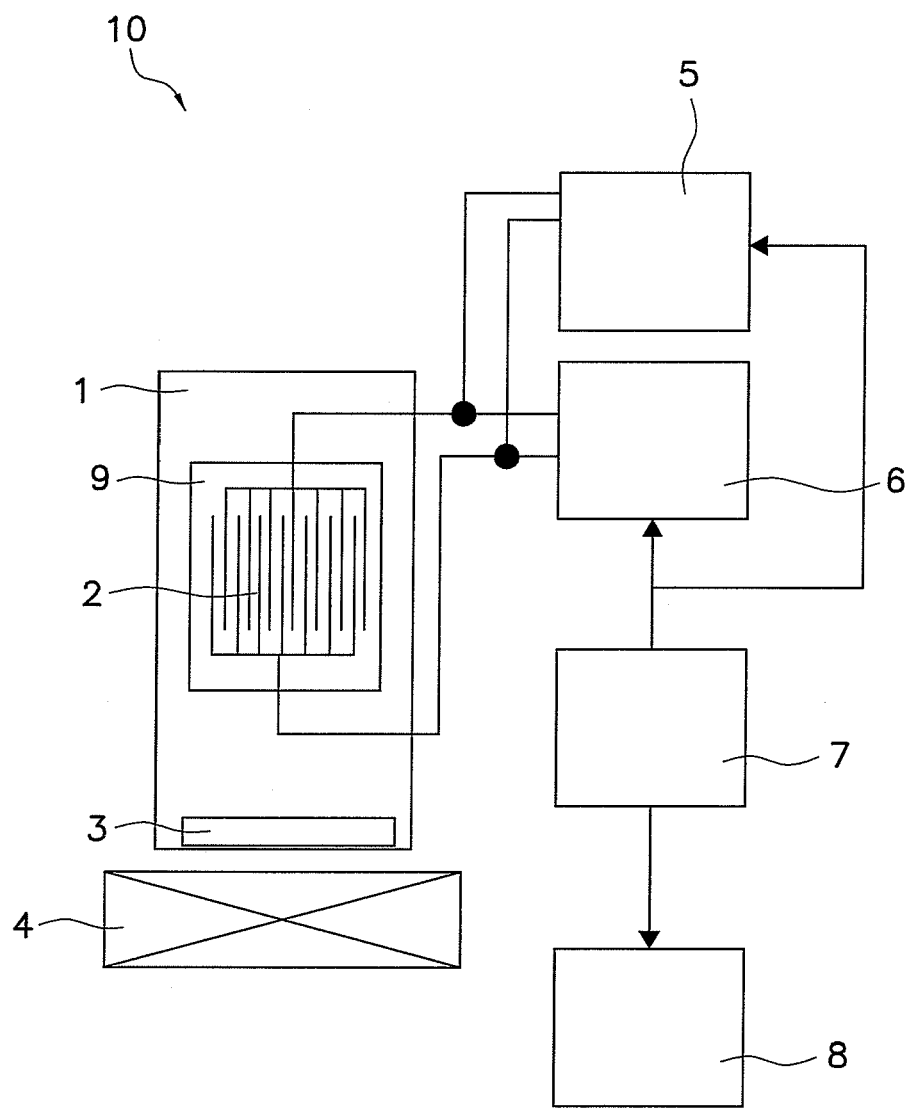
FIG. 1 is a concept diagram illustrating the configuration of the microbe testing device pertaining to an embodiment of the present invention.

The microbe testing device 10 pertaining to the this embodiment is a testing device for detecting microbes (microorganisms) present in the oral cavity and collected with a sample collector 13 (see FIG. 6), for example. As shown in FIG. 1, this device comprises a measurement cell (case) 1, an electrode substrate 9 including a thin-film electrode 2 (electrode portion), a rotor 3, a stator 4, a power supply 5, a measurement portion 6, a controller 7, and a display portion 8.

Figure 2:
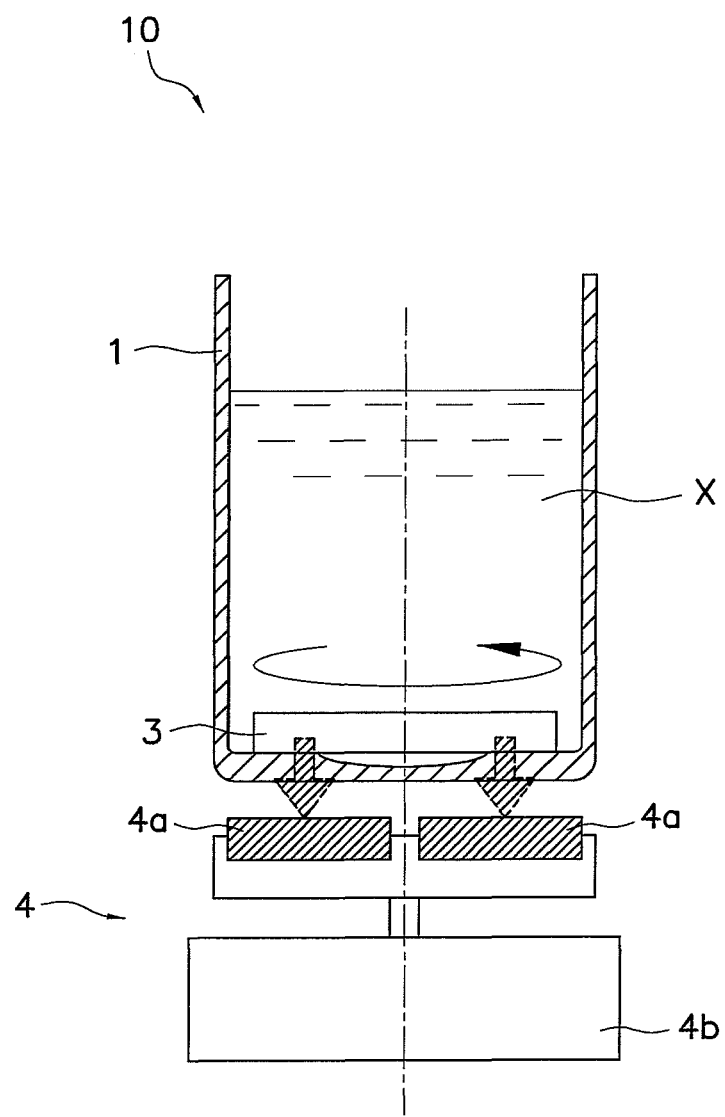
FIG. 2 is a front view illustrating the configuration around a measurement cell included in the microbe testing device shown in FIG. 1.

The measurement cell 1 is a cylindrical, glass vessel having a sidewall and a bottom face 11b having a sidewall and a bottom face 11b for holding a sample liquid X (see FIG. 2). The bottom face 11b includes a concave portion 11a surrounded by a ledge portion 11c (see FIGS. 3A and 3B). The rotor 3, which is used to stir the sample liquid X, is placed in the measurement cell 1. The rotor 3 rotates while linked via magnetic force to the stator 4, which is disposed near the bottom face 11b (inner wall face) of the measurement cell 1 (see FIG. 3A). Accordingly, glass, which does not block magnetic force, is used as the measurement cell 1. In addition to glass, the material of the measurement cell 1 can also be a plastic or the like. The detailed configuration of the measurement cell 1 will be discussed at a later stage.

Any of various liquids can be used as the sample liquid X held in the measurement cell 1, examples of which include water, oils, ethanol and other alcohols, acetone, DIMSO, furan, and other organic solvents, and mixtures of these.

The thin-film electrode 2 is used to detect microbes (microorganisms) by moving the microbes to a specific location in the sample liquid by electrophoresis, and comb-like electrodes are disposed opposite each other with a microscopic gap in between. The size of this microscopic gap is from 5 to 20 μm. The thin-film electrode 2 is formed by covering the electrode substrate 9 with a conductive material by sputtering, vapor deposition, plating, or another such method. When voltage is applied to this thin-film electrode 2, the electrical field is strongest near the microscopic gaps constituted by the comb-like intersecting portions of the thin-film electrode 2. The microbes (microorganisms) migrate toward these microscopic gaps where the electrical field is most concentrated. Also, the electrode substrate 9, on the surface of which is formed the thin-film electrode 2, is attached to the side wall face of the measurement cell 1.

Figure 3A:
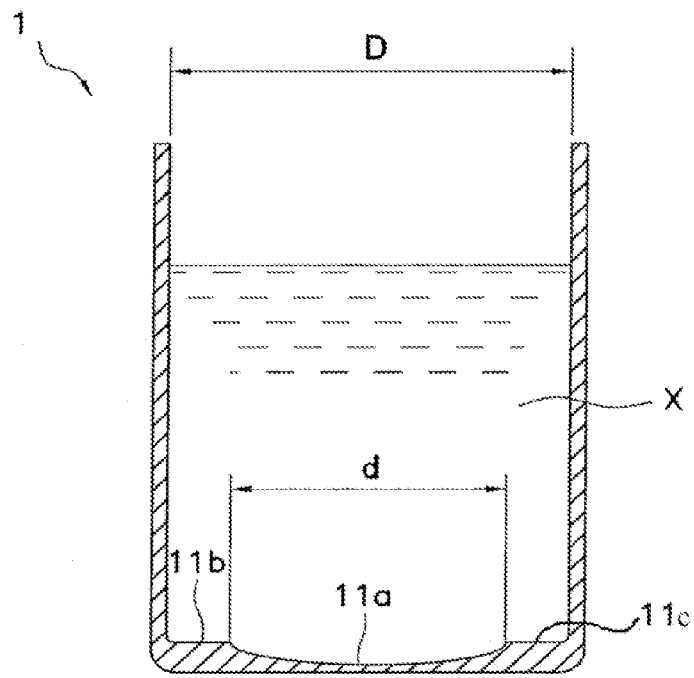
FIGS. 3a and 3b are a front view and a plan view of the shape of the measurement cell in FIG. 1.

As shown in FIG. 2, the rotor 3 is a metal member having a substantially cylindrical shape, and is rotated along the bottom face 11b of the measurement cell 1 by magnetic force imparted from the stator 4, which is disposed near the bottom face 11b of the measurement cell 1 (see FIG. 3A). The relationship between the rotor 3 and the bottom face 11b (inner wall face) of the measurement cell 1 (see FIGS. 3A and 3B) will be discussed at a later stage.

As shown in FIG. 2, the stator 4 has a rotatable magnet 4a disposed across from the bottom face 11b of the measurement cell 1, and imparts magnetic force (attractive force) in the direction of the arrow in the drawing to the metal rotor 3. Also, when the stator 4 is attracting the rotor 3, rotating the magnet 4a with a motor 4b will rotate the rotor 3 in the sample liquid X. Consequently, the sample liquid X is stirred by the rotor 3 inside the measurement cell 1.

The power supply 5 applies AC voltage to the thin-film electrode 2 in order to produce electrophoresis. The "AC voltage" referred to here is voltage with a sine wave, or any voltage that changes the direction of flow at a substantially constant period, and includes voltage in which the average values of this bidirectional current are equal. In this embodiment, AC voltage with a frequency of 100 kHz and a peak-to-peak (hereinafter referred to as pp) voltage of 5 V is applied. The voltage value and frequency of the AC voltage are not limited to the values given above, and a numerical value can be selected from a wide range of from 100 Hz to 50 MHz, for example, according to the type of microorganisms and the sample liquid conditions.

The measurement portion 6 is constituted so as to include a microprocessor (not shown), a memory for temporarily storing measurement data and so forth, etc. The measurement portion 6 detects the microbe count in the sample liquid by detecting changes in impedance in the thin-film electrode 2.

The controller 7 is constituted so as to include a microprocessor (not shown), a memory for storing a preset program, a timer, control buttons, and so forth. The controller 7 controls the power supply 5 so as to apply voltage to the thin-film electrode 2 for electrophoresis according to the preset program. Also, the controller 7 sends and receives signals between to and from the measurement portion 6, and controls the display portion 8 so as to display measurement results, operating status, and so forth.

The display portion 8 is an LCD or other such display, or a printer, speaker, or the like, and displays the microorganism count in the sample liquid, which means an indicator of the state of oral hygiene, as the evaluation result.

Shape of Measurement Cell 1

Figure 3B:
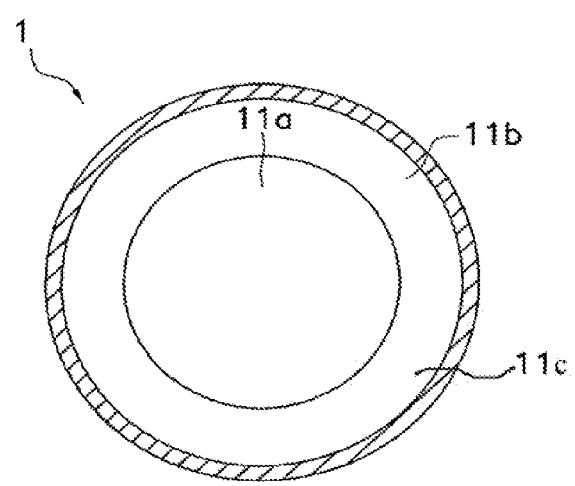

With the microbe testing device 10 in this embodiment, as shown in FIGS. 3A and 3B, a concave portion 11a is formed in the approximate middle of the bottom face 11b of the measurement cell 1 that holds the sample liquid X.

As shown in FIG. 3B, the concave portion 11a is a depression formed in a substantially circular shape (in plan view) in the substantially circular bottom face 11b, and is provided so that the rotor 3 and the bottom face 11b will be in contact only at the end portions of the rotor 3. Consequently, since the stator 4 applies magnetic force (attractive force) to the rotating rotor 3, creating friction force between the rotor 3 and the bottom face 11b, the rotor 3 can be rotated in a stable state while being supported at its two ends.

Also, as shown in FIG. 3A, the concave portion 11a is formed such that its diameter d satisfies the following relational Formula 1 with respect to the diameter D of the bottom face 11b.

$$0.3D \leq d \leq 0.9D \quad (1)$$

As a result, the contact surface area between the bottom face 11b and the ends of the rotor 3 can be set to a suitable value according to all the prevailing conditions, such as the viscosity of the sample liquid X and whether or not there is contact with a sample collector 13. Thus, the rotor 3 can be rotated in a stable state while a suitable amount of frictional resistance is imparted to the rotating rotor 3.

Figure 4:
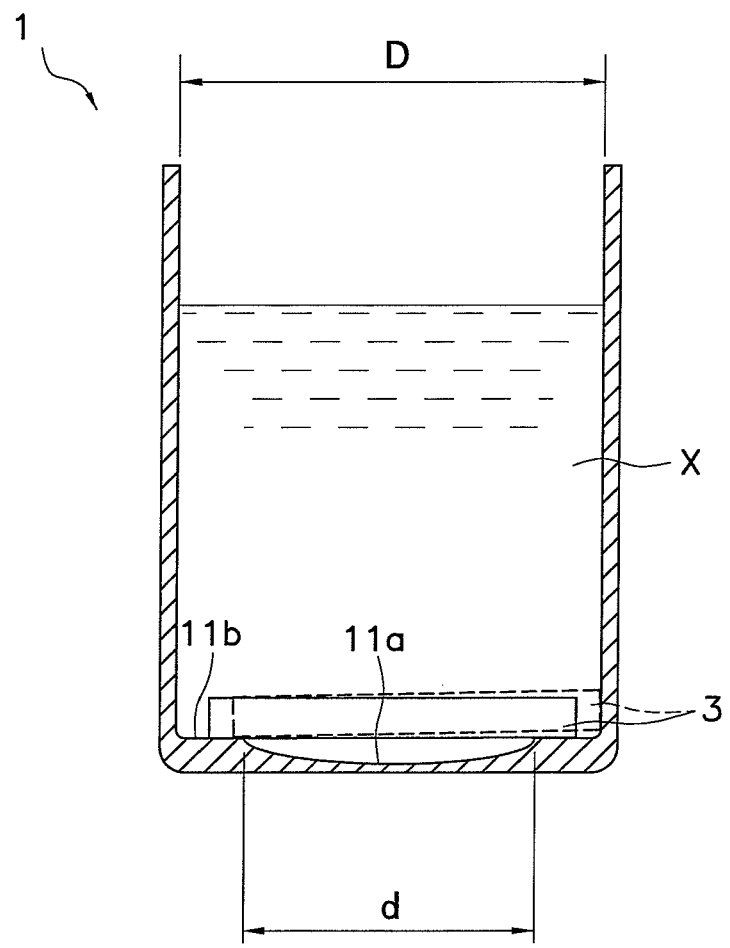
FIG. 4 is a front view of the relationship between the size of the concave portion and the position of the rotor in the measurement cell in FIG. 1.

Further, as shown in FIG. 4, the diameter of the concave portion 11a is set so that, with respect to the axial length of the substantially cylindrical rotor 3, in a state in which one end of the rotor 3 has moved all the way to the edge of the bottom face 11b (see the dotted line in the drawing), the other end of the rotor 3 will not fall into the concave portion 11a.

Consequently, the rotation of the rotor 3 can be started more smoothly because the rotor 3 is always in a state of being disposed over the bottom face 11b.

Flow from Sample Collection to Microbe Detection

The flow of the process from the collection of a sample with the sample collector 13 up to the measurement of microbes (microorganisms) in the sample liquid and evaluation of the hygienic state in the oral cavity will now be described through reference to the flowchart of FIG. 5, and to FIG. 6.

Figure 5:
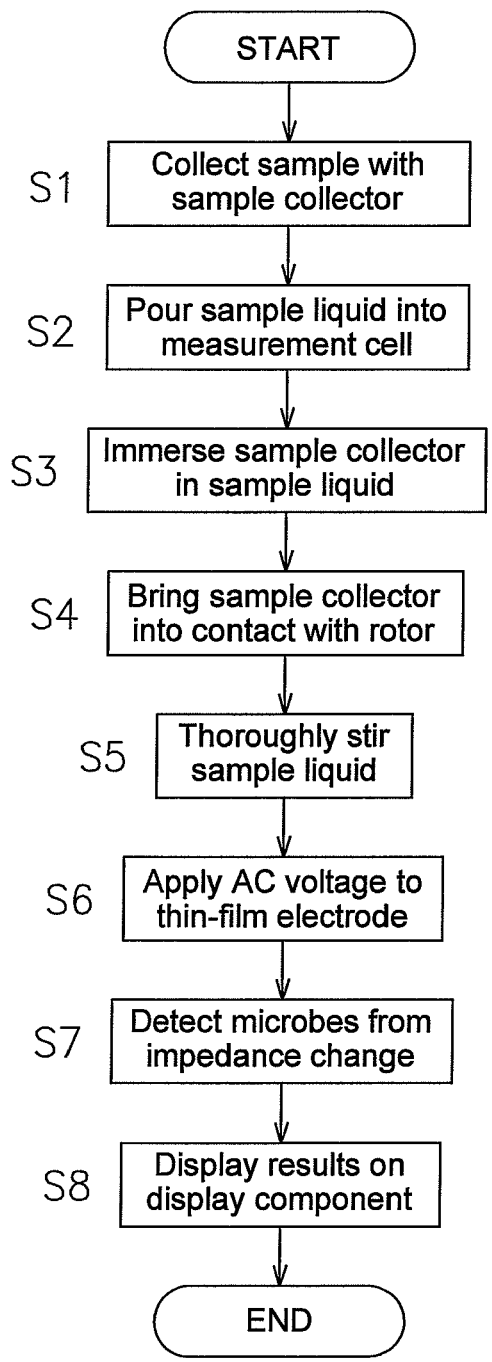
FIG. 5 is a flowchart of the flow from the collection of microbes to their measurement using the microbe testing device in FIG. 1.

As shown in FIG. 5, first, in step S1, the sample collector 13 (a cotton swab or the like) is used to collect a sample (microbes) from the oral cavity. Examples of the sample taken from the oral cavity of the test subject include a cloth or cotton swab that has been rubbed against the oral cavity wall, the tongue, or the teeth; saliva or a cloth that has been soaked with saliva; and a sample scraped with a pick-like tool from between the teeth. The sample used to evaluate the hygienic state in the oral cavity in this embodiment was obtained by wiping the tooth surfaces with a cotton swab or other such sample collector 13.

More specifically, sample collection in this embodiment is performed by having the test subject himself hold a cotton swab and wipe the surface of his teeth at the measurement site. When the sample is collected from a specific tooth surface, the hygienic state at that site is evaluated, but when overall collection is performed, the state of the oral cavity is evaluated comprehensively.

Next, while the above-mentioned sample collection is being performed, in step S2 the sample liquid X is poured into the measurement cell 1 in preparation for measurement and evaluation.

Next, in step S3 (first step) the distal end 13a of the sample collector 13 that has collected a sample from the oral cavity is immersed in the sample liquid X (see FIG. 6), and the microbes are suspended in the sample liquid X.

Figure 6:
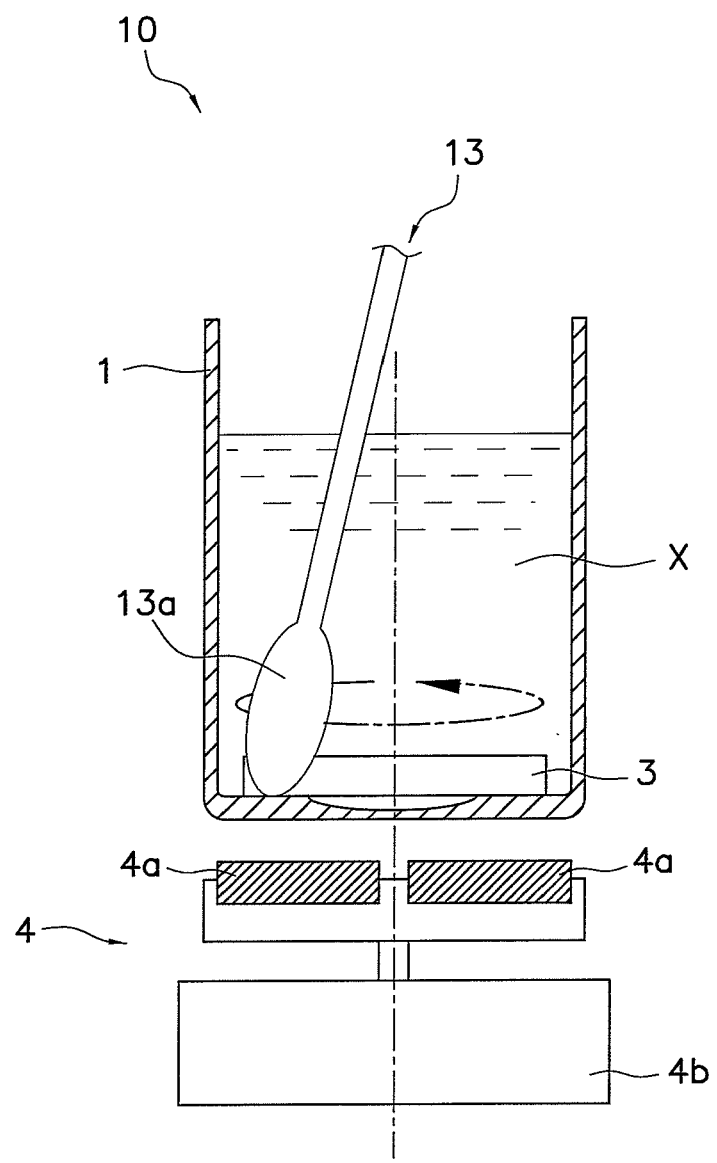
FIG. 6 is a front view of a state in which a cotton swab has been inserted into a sample liquid held in the measurement cell in FIG. 1.

Next, in step S4 (second step), as shown in FIG. 6, the distal end 13a of the sample collector 13 immersed in the sample liquid X is brought into contact with the rotor 3 that is rotating in the sample liquid X. This operation is carried out to effectively suspend the microbes or other sample collected at the distal end 13a of the sample collector 13 in the sample liquid X.

Here, the concave portion 11a is formed in the approximate middle of the bottom face 11b of the measurement cell 1. Accordingly, the rotor 3 rotates while in contact only at its end portions with the bottom face 11b. Thus, even when the cotton swab or other sample collector 13 is brought into contact with the rotor 3 in the sample liquid X, the ends of the rotor 3 are supported by the bottom face 11b, so friction with the bottom face 11b causes less loss of rotational balance.

Next, in step S5 (third step) the rotor 3 is rotated by the stator 4, and the sample liquid X in which the microbes, etc., have been released from the distal end 13a of the sample collector 13 is thoroughly stirred.

Next, in step S6 the controller 7 controls the power supply 5 so that AC voltage is applied to the thin-film electrode 2 on the electrode substrate 9 disposed on the side wall face of the measurement cell 1.

Next, in step S7 (fourth step) the microbe count in the sample liquid X is detected by detecting the change in impedance in the thin-film electrode 2 in the measurement portion 6.

Next, in step S8 the controller 7 ends processing after displaying the detection result from the measurement portion 6 on the display portion 8.

In this embodiment, the procedure goes through the above steps to carry out everything from sample collection with the sample collector 13, to the release of microbes into the sample liquid X, the stirring of the sample liquid X, and microbe detection.

Consequently, a single microbe testing device 10 can be used to perform all the steps from the effective release and suspension of the collected microbes into the sample liquid X, to the detection of the released microbes. Thus, the above steps can be completed without having to use a separate suspension apparatus for suspending the sample liquid X, which means that the process is much more efficient than with a conventional process.

Features of this Microbe Testing Device 10

(1)

As shown in FIG. 2, the microbe testing device 10 in this embodiment is equipped with the measurement cell 1 that holds the sample liquid X, and the rotor 3 that is rotated along the bottom face 11b in the sample liquid X held in the measurement cell 1, by magnetic force imparted from outside the measurement cell 1. The rotor 3 stirs the sample liquid X by rotating while only its end portions are in contact with the bottom face 11b of the measurement cell 1.

Consequently, the rotor 3 can be rotated along the bottom face 11b in a state of only its end portions being in contact with the bottom face 11b. This means that the rotating rotor 3 is supported at its two ends, and frictional resistance can be produced at the portions of contact with the bottom face 11b. As a result, this avoids rotational imbalance of the rotor 3 in the sample liquid X that would otherwise be caused by external factors in the sample liquid X, and allows the stirring of the sample liquid X (suspension of the microbes) to be carried out more effectively in the measurement cell 1.

(2)

With the microbe testing device 10 in this embodiment, as shown in FIGS. 3A and 3B, the concave portion 11a is provided at a location of the bottom face 11b on which the rotor 3 is rotating in the measurement cell 1, which encompasses the rotational center of the rotor 3 in plan view.

Consequently, a mode in which only the end portions of the rotor 3 come into contact with the bottom face 11b, which is necessary to avoid rotational imbalance of the rotor 3, can be achieved with a simple constitution. This means that a device having stable stirring performance can be obtained merely by modifying the shape of the bottom face 11b of the measurement cell 1.

(3)

With the microbe testing device 10 in this embodiment, as shown in FIG. 4, even when the rotor 3 has moved to an offset location along the bottom face 11b within the measurement cell 1, the concave portion 11a is formed in a size such that the end of the rotor 3 on the opposite side from the offset end will not fall in.

Consequently, the rotation of the rotor 3 can be started extremely smoothly by employing a measurement cell 1 (concave portion 11a and bottom face 11b) of optimal size, according to the axial length of the substantially cylindrical rotor 3. Also, if the sample collector 13 or the like should come into contact with the rotating rotor 3, it will still be possible to avoid a situation in which the rotor 3 becomes unbalanced and one end falls into the concave portion 11a, rendering rotation impossible.

(4)

With the microbe testing device 10 in this embodiment, as shown in FIG. 3A, etc. the bottom face 11b of the measurement cell 1 forms a substantially circular bottom portion, and the diameter d of the concave portion 11a is designed to satisfy the following Relationship Formula 1 with the diameter D of the substantially circular bottom face 11b.

$$0.3D \leq d \leq 0.9D \quad (1)$$

Consequently, the contact surface area between the bottom face 11b and the ends of the rotor 3 can be adjusted by setting the size of the concave portion 11a. As a result, the rotor 3 can be stably rotated in the measurement cell 1 while a suitable amount of frictional resistance is imparted to the rotor 3.

(5)

As shown in FIG. 1, in addition to the function of a stirring device that rotates the rotor 3 and stirs the sample liquid X, the microbe testing device 10 in this embodiment also is equipped with the thin-film electrode 2, which is provided in the measurement cell 1 and to which voltage is applied for measurement by electrophoresis of the microbes in the sample liquid X.

Consequently, microbes contained in the sample liquid X, which has been thoroughly stirred by the rotor 3, can be detected more accurately by the thin-film electrode 2.

(6)

With the microbe testing device 10 in this embodiment, as shown in FIG. 6, the sample collector 13 that has collected microbes is brought into contact with the rotor 3 that is rotating in the sample liquid X.

Consequently, when the rotor 3 that is supported at its end portions by the bottom face 11b hits the distal end 13a of the sample collector 13, the microbes, etc., collected at the distal end 13a are effectively released into the sample liquid X. As a result, the sample liquid X can be thoroughly stirred by the rotor 3, and microbes can be efficiently detected at the thin-film electrode 2.

(7)

As shown in FIG. 5, the microbe testing method in this embodiment comprises a step of immersing the distal end 13a of the sample collector 13, which has collected a sample of the oral cavity, into the sample liquid X, a step of hitting the distal end 13a of the sample collector 13 with the rotating rotor 3 in the sample liquid X, a step of stirring the microbes released from the distal end 13a of the sample collector 13 in the sample liquid X with the rotor 3, and a step of detecting the microbes stirred in the sample liquid X.

Consequently, the microbes collected by the sample collector 13 are effectively suspended in the sample liquid X, and the effectively suspended microbes in the sample liquid X are accurately detected. As a result, single microbe testing device 10 can be used to perform all the steps from suspension of the microbes in the sample liquid X to their detection, so no separate suspension apparatus or the like has to be used, and the process can be simplified.

(8)

With the microbe testing method in this embodiment, as shown in FIG. 2, etc., only the end portions of the rotor 3 are brought into contact with the bottom face 11b of the measurement cell 1 when the rotor 3 is rotated in the measurement cell 1.

Consequently, even if the sample collector 13 comes into contact with the rotating rotor 3 in the step of hitting the sample collector 13 with the rotor 3, because the ends of the rotor 3 are supported by the bottom face 11b, and the frictional resistance becomes a repulsive force at the bottom face 11b, loss of balance can be kept to a minimum in the rotor 3. Thus, even when a step is included for bringing the rotor 3 into contact with the sample collector 13, the sample liquid X can still be thoroughly stirred by the rotor 3.

(9)

With the microbe testing method in this embodiment, as shown in FIG. 6, a cotton swab is used as the sample collector 13 that is immersed in the sample liquid X to collect microbes from the oral cavity.

Consequently, by using a readily available and simple tool such as the sample collector 13, the process from collection of microbes to their stirring into the sample liquid X can be carried out inexpensively and easily.

Other Embodiments

An embodiment of the present invention was described above, but the present invention is not limited to the above embodiment, and various modifications are possible without departing from the scope of the invention.

(A)

In the above embodiment, as shown in FIG. 2, etc., an example in which the concave portion 11a was provided in the approximate middle of the bottom face 11b of the measurement cell 1 was described as a mode in which the end portions of the rotor 3 were the only contact portion between the bottom face 11b of the measurement cell 1 and the rotor 3. However, the present invention is not limited to this.

Figure 7:
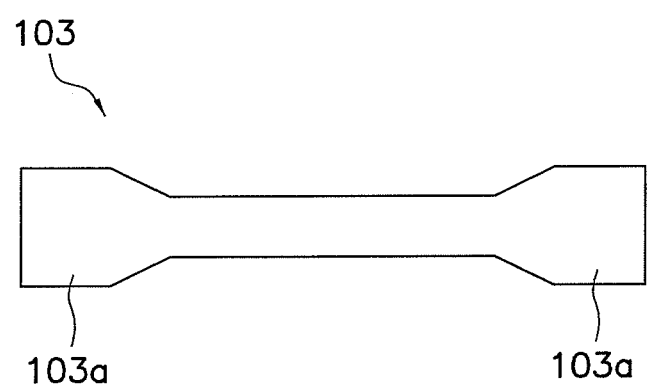
FIG. 7 is a front view of the configuration of a rotor included in the stirring device pertaining to another embodiment of the present invention.

For instance, as shown in FIG. 7, a rotor 103 may be rotated along the bottom face of an ordinary flat measurement cell, using a rotor 103 having a large diameter portion 103a at the left and right ends.

In this case, the shape of the rotor 103 can create a mode in which only the end portions of the rotor 103 come into contact with the bottom face of the measurement cell.

The large diameter portion 103a may, for example, be formed by integral molding as the rotor 103, or if the rotor is relatively large, it may be formed by separate molding at the end portions of a substantially cylindrical rotor by a method such as embedding screws.

(B)

In the above embodiment, as shown in FIG. 2, etc., an example was described in which the rotor 3 rotated on the bottom face of the measurement cell 1, but the present invention is not limited to this.

For instance, besides the bottom face, the inner wall face on which the rotor is rotated may be the side face of the measurement cell, etc.

In this case, the rotor can be moved to the side wall by the attractive force of a magnet, and rotated in this state so that the rotor is rotated along the side wall face.

(C)

In the above embodiment, as shown in FIG. 3B, etc., an example was described in which a substantially circular (in plan view) concave portion 11a was formed in the bottom face of the substantially circular measurement cell 1, but the present invention is not limited to this.

For instance, besides being substantially circular, the shape of the bottom face of the measurement cell, and the shape of the concave portion may be polyhedral, or may be elliptical.

However, employing the shape used in the above embodiment is preferable in that will be easier to stably rotate a measurement cell having a concave portion or bottom face whose shape matches the rotational path of the rotor.

(D)

In the above embodiment, as shown in FIG. 3A, etc., an example was described in which the concave portion 11a formed on the bottom face of the measurement cell 1 was formed along a smooth curve as seen in front view, but the present invention is not limited to this.

For instance, a concave portion that does not touch the rotor does not necessarily have to have a smooth curve, and may have a somewhat bumping face.

(E)

In the above embodiment, an example was described in which the stirring device pertaining to the present invention was applied to the microbe testing device 10, but the present invention is not limited to this.

For instance, the present invention may be applied to a testing device other than a microbe testing device, or may be applied to a simple stirring device.

INDUSTRIAL APPLICABILITY

With the stirring device of the present invention, the rotor has better balance during rotation than with a conventional stirring device in which the rotor is rotated around a convex portion formed on an inner wall face of the case, the effect of which is that the sample liquid can be thoroughly stirred regardless of the sample liquid conditions, etc., so this stirring device can be applied to a wide range of testing devices and so forth in which stirring is accomplished with a rotor.

What is claimed is:

1. A stirring device comprising:
a case for holding a sample liquid, the case having a sidewall and a bottom face with a concave portion and a ledge portion completely surrounding the concave portion; and
a rotor that stirs the sample liquid by being rotated by magnetic force, imparted from outside the case, along the ledge portion of the case in the sample liquid held inside the case, with only a first end portion and a second end portion, which is opposite to the first end portion, of the rotor coming into contact with the ledge portion of the case,
wherein the concave portion of the bottom face is formed around a central axis of the bottom face,
wherein the ledge portion extends from the sidewall to the concave portion, and
wherein a width of the ledge portion between a first portion of the sidewall and the concave portion along a straight line that passes through the first portion of the sidewall, the central axis of the bottom face and a second portion of the sidewall, which is on an opposite side of the central axis of the bottom face than the first portion of the sidewall, is larger than a gap formed between the first end portion of the rotor and the first portion of the sidewall when the rotor is coaxial with the straight line and the second end portion of the rotor is in contact with the second portion of the sidewall.

2. The stirring device according to claim 1,
wherein the bottom face is substantially circular, and
the concave portion is formed so that its diameter d satisfies the following Relational Formula 1 with a diameter D of the substantially circular bottom face $$0.3D \leq d \leq 0.9D \tag{1}.$$

3. The stirring device according to claim 1,
wherein the rotor has a large diameter portion at both end portions.

4. A microbe testing device comprising:
the stirring device according to claim 1; and
an electrode portion provided inside the case, to which is applied voltage for measuring microbes in the sample liquid by electrophoresis.

5. The microbe testing device according to claim 4, further comprising a sample collector that comes into contact with the rotor that is rotating in the sample liquid, and suspends the microbes in the sample liquid.

6. The stirring device according to claim 2,
wherein the rotor has a large diameter portion at both end portions.

7. A microbe testing device comprising:
the stirring device according to claim 2; and
an electrode portion provided inside the case, to which is applied voltage for measuring microbes in the sample liquid by electrophoresis.

8. A microbe testing device comprising:
the stirring device according to claim 3; and
an electrode portion provided inside the case, to which is applied voltage for measuring microbes in the sample liquid by electrophoresis.

9. The stirring device according to claim 1, wherein the width of the ledge portion is constant between the sidewall and the concave portion along any line that extends radially from and perpendicular to the central axis of the bottom face.

10. The stirring device according to claim 1, wherein the ledge portion extends along a single plane.

* * * * *